United States Patent [19]
Graves et al.

[11] Patent Number: 5,972,095
[45] Date of Patent: *Oct. 26, 1999

[54] FAST DRYING NAIL ENAMEL COMPOSITION AND METHOD

[75] Inventors: Gary G. Graves, Germantown, Tenn.; Terry C. Jacks, Olive Branch, Miss.

[73] Assignee: Maybelline Cosmetics Corporation, Wilmington, Del.

[ * ] Notice: This patent is subject to a terminal disclaimer.

[21] Appl. No.: 09/045,029

[22] Filed: Mar. 20, 1998

Related U.S. Application Data

[63] Continuation of application No. 08/881,236, Jun. 24, 1997, Pat. No. 5,766,332, which is a continuation of application No. 08/560,542, Nov. 17, 1995, Pat. No. 5,688,494.

[51] Int. Cl.⁶ ..................... A61K 7/043; C09D 183/10
[52] U.S. Cl. ................... 106/287.11; 106/287.13; 106/287.14; 106/287.15; 106/287.16; 106/169.13; 106/169.17; 106/170.14; 106/170.2; 106/174.1; 106/177.1; 106/203.1; 106/203.2; 424/61; 424/78.02

[58] Field of Search .............. 106/287.11, 287.13, 106/287.14, 287.15, 287.16, 169.13, 169.17, 170.14, 170.2, 174.1, 177.1, 203.1, 203.2; 424/61, 78.02

[56] References Cited

U.S. PATENT DOCUMENTS

| | | |
|---|---|---|
| 4,158,053 | 6/1979 | Greene et al. . |
| 5,032,460 | 7/1991 | Kantner et al. ................ 428/449 |
| 5,342,872 | 8/1994 | Huber . |
| 5,468,477 | 11/1995 | Kumar et al. ................ 424/78.17 |
| 5,538,717 | 7/1996 | La Poterie . |
| 5,571,858 | 11/1996 | de La Poterie et al. . |
| 5,601,808 | 2/1997 | Mellul et al. . |
| 5,688,494 | 11/1997 | Graves et al. ................ 424/61 |
| 5,725,882 | 3/1998 | Kumar et al. ................ 424/486 |

*Primary Examiner*—David Brunsman
*Attorney, Agent, or Firm*—Sherman and Shalloway

[57] ABSTRACT

A nail enamel based on a solvent mixture of nitrocellulose, and plasticizer(s) is made faster drying by incorporating a particular class of vinyl-silicone copolymers. Trapping of bubbles in the dried enamel is avoided by incorporating a dimethicone anti-foaming agent.

13 Claims, No Drawings

FAST DRYING NAIL ENAMEL COMPOSITION AND METHOD

CROSS-REFERENCE TO RELATED APPLICATIONS

This application is a continuation of application Ser. No. 08/881,236, filed Jun. 24, 1997, now U.S. Pat. No. 5,766,332, issued Jun. 16, 1998, which in turn is a continuation of application Ser. No. 08/560,542, filed Nov. 17, 1995, now U.S. Pat. No. 5,688,494, issued Nov. 18, 1997.

BACKGROUND OF THE INVENTION

1. Field of the Invention

This invention relates to the field of enamel coating compositions for application to human nails. More particularly, this composition relates to a nail enamel composition which is quick drying.

2. Discussion of the Prior Art

There have been many attempts to shorten the time required to apply nail enamel and allow the enamel to dry at and below the surface so that the user is not impeded from going about her normal business without risk of smudging, streaking, marring, smearing or, indeed, transferring the enamel to clothing, etc. Furthermore, such quick drying must not be at the expense of wearing properties, gloss, hardness or-washability. Suitably 1–4 minutes is considered to be a desirable fast drying time.

While several of these attempts, usually based on such factors as solvent system, curing system, or film-forming resin system, have met with limited success, still further improvements are desired for reduction in drying time and quality of the dried enamel.

Accordingly, it is an object of the invention to provide a fast drying nail polish enamel which is capable of effectively drying in a very short time.

SUMMARY OF THE INVENTION

In an effort to achieve the above stated object an attempt was made to incorporate in an appropriate fast drying nail enamel base formula a vinyl-silicone copolymer which had been described as able to produce a continuous film immediately upon application. This vinyl-silicone copolymer is described, for example, in U.S. Pat. No. 5,032,460 to Kanter, et al., and assigned to Minnesota Mining and Manufacturing Company (3M) and in 3M's published International Application WO 93/23009. It was found that when a vinyl-silicone copolymer according to these 3M patent documents was added to a nail enamel composition including a nitrocellulose film former and other secondary film forming agents the drying time was reduced. Moreover, adding a non-polar hydrocarbon solvent to the formulation may allow the vinylsilicon copolymer to come to the surface faster and further enhance the fast drying effect.

However, it was consistently found that when the fast drying enamel composition was applied to nails severe bubbling occurred. The bubbling results in non-uniformities in the dried enamel coating which so adversely effect the appearance that the product was not commercially viable or useful.

Accordingly, attempts were made to overcome the bubbling phenomenon by incorporating commercially available anti-foaming agents into the composition. While some products were found which reduced the bubbling some bubbling still occurred or large amounts of anti-foaming agent was requires.

The present invention is, therefore, based on the discovery that a fast drying and non-bubbling nail enamel coating which is based on the incorporation of a fast drying vinyl-silicone copolymer resin into a nitrocellulose-based nail enamel composition is provided by further adding to the composition a minor amount of a polydimethylsiloxane (dimethicone) antifoaming agent having a viscosity in the range of about 200 to 500 centistokes (cSt).

Accordingly, the present invention provides a fast drying non-bubbling nail enamel composition which includes a solvent solution of a plasticized film-forming cellulose derivative; vinyl-silicone graft or block copolymer comprising a silicone polymer segment and a vinyl polymer segment; and dimethicone anti-foaming agent.

DETAILED DESCRIPTION OF THE INVENTION AND PREFERRED EMBODIMENTS

As used herein the term "dry" as applied to fast drying refers to throughout the thickness of the applied coating and not merely to the surface. That is, it is not considered sufficient for the enamel coating to feel "dry to the touch" while retaining solvent in lower layers. Such "dry to the touch" coatings are still subject to damage or marring when the coated nail brushes up against a hard surface.

Also, the fast dry nail enamel compositions of this invention may be formulated to provide a clear or transparent hard, glossy enamel coating or may include pigment or other coloring agent to provide a colored hard, glossy enamel coating. The clear or transparent coating may be and, preferably is, applied directly to the nails but may also be applied over a previously applied coating of a colored nail polish. The colored nail enamel is intended to be applied directly to the nails and does not require any other under- or over-coating.

The compositions of this invention include the following essential components typically found in nail enamel compositions: solvents; film-forming agents; plasticizer(s) for the film-forming agents; thickener(s) or thixotropic agent(s) to impart sufficient viscosity so that the composition may be easily applied to the nails but not run-off regardless of the position of the nails. The composition may also include one or more additional additives for functional or aesthetic attributes, such as, for example, pigments and other coloring agents, preservatives and perfumes.

The compositions of this invention are, however, particularly characterized by the combination of the fast drying vinyl-silicone graft or block copolymer to be described below; and dimethicone anti-foaming agent to effectively prevent bubbling during drying of the enamel coating. These various essential and preferred ingredients will now be described.

The vinyl-silicone graft or block copolymer, which is described in detail in 3M's U.S. Pat. No. 5,032,460 and WO 93/23009, the disclosures of which are incorporated herein in their entirety by reference thereto, has the following general formula:

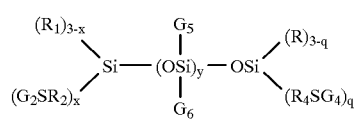

wherein $G_5$ represent monovalent moieties which can independently be the same or different selected from the group consisting of alkyl, aryl, alkaryl, alkoxy, alkylamino; fluoroalkyl, hydrogen, and -ZSA; A represents a vinyl polymeric segment consisting essentially of polymerized free radically polymerizable monomer and Z is a divalent linking group. Useful divalent linking groups Z include but are not limited to the following: $C_1$ to $C_{10}$ alkylene, alkarylene, arylene, and alkoxyalkylene. Preferably, Z is selected from methylene and propylene for reasons of commercial availability.

$G_6$ represents monovalent moieties which can independently be the same or different selected from the group consisting of alkyl, aryl, alkaryl, alkoxy, alkylamino, fluoroalkyl, hydrogen and -ZSA;

$G_2$ comprises A;
$G_4$ comprises A;

$R_1$ represents monovalent moieties which can independently be the same or different and are selected from alkyl, aryl, alkaryl, alkoxy alkylamino, fluoroalkyl, hydrogen, and hydroxyl. Preferably, $R_1$ represents monovalent moieties which can independently be the same or different selected from $C_{1-4}$ alkyl and hydroxyl for reasons of commercial availability. Most preferably, $R_1$ is methyl.

$R_1$ can independently be the same or different and represents divalent linking groups. Suitable divalent linking groups include but are not limited to the following: $C_1$ to $C_{10}$ alkylene, arylene, alkarylene, and alkoxyalkylene. Preferably, $R_2$ is selected from $C_{1-3}$ alkylene and $C_{7-10}$ alkarylene due to ease of synthesis of the compound. Most preferably, $R_2$ is selected from —$CH_2$—, 1,3-propylene, and

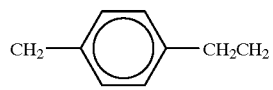

$R_3$ represents monovalent moieties which can independently be the same or different and are selected from alkyl, aryl, alkaryl, alkoxy, alkylamino, fluoroalkyl, hydrogen, and hydroxyl. Preferably $R_3$ represents monovalent moieties which can independently be the same or different $C_{1-4}$ alkyl and hydroxyl for reasons of commercial availability. Most preferably, $R_3$ is methyl.

$R_4$ can independently be the same or different divalent linking groups. Suitable divalent linking groups include but are not limited to the following: $C_1$ to $C_{10}$ alkylene, arylene, alkarylene and alkoxyalkylene. Preferably, $R_4$ is selected from $C_{1-3}$ alkylene and $C_{7-10}$ alkarylene for reasons of ease of synthesis. Most preferably, $R_4$ is selected from —$CH_2$—, 1,3-propylene, and

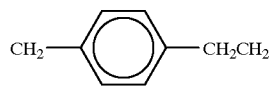

x is an integer of 0–3;
y is an integer of 5 or greater; preferably, y is an integer ranging from about 10 to about 270 in order to provide the silicone segment with a molecular weight ranging from about 750 to about 20,000. Most preferably, y is an integer ranging from about 40 to about 270;
q is an integer of 0–3.
Furthermore, at least one of the following is true;
q is an integer of at least 1;
x is an integer of at least 1;

$G_5$ comprises at least one -ZSA moiety;
$G_6$ comprises at least one -ZSA moiety.

For further details on these copolymers, including each of the vinyl polymeric segments and silicone polymeric segments, the reactants therefore, and the polymerization techniques, reference is made to the aforementioned patent documents to 3M, which are incorporated herein by reference. It should be noted, in particular, that WO 93/23009 on pages 29–31 recognize that a cosmetic composition prepared by dissolving the vinyl-silicone copolymer into a low-boiling point oil or volatile solvent produce a cosmetic film exhibiting superior water-resistance, oil-resistance, and may be applied to nails, such as a nail enamel. The low-boiling point oil may be a volatile hydrocarbon oil having a boiling point below 260° C., at normal pressure. The volatile solvent may be linear, cyclic, or branched silicone oil having a boiling point below 260° C. at normal pressure and a viscosity below 10 cSt. It is further mentioned that hard films can be produced by introducing a large amount of monomers such as methylmethacrylate, t-butyl(meth)acrylate, isobutylmethacrylate, etc. into acrylic chains. The amount of copolymer in the disclosed film-forming cosmetic composition is from 0.03 to 70% by weight; and, conversely, from 99.97 to 30% by weight of volatile solvent.

In the present invention the vinyl-silicone copolymer is incorporated into the composition in a range of about 0.1 to 5% by weight, preferably 0.25 to 2.0% by weight, and most preferably 0.5 to 1.0% by weight.

A volatile non-polar aliphatic hydrocarbon solvent, such as heptane, may be included in the composition of this invention in order to promote the rapid drying of the composition. Although not wishing to be bound by any theory of operation, it is believed that as the other solvents evaporate, the non-polar hydrocarbon promotes the migration of the vinyl-silicone copolymer to the surface of the enamel coating to enhance the fast dry effect.

The amount of the particular non-polar aliphatic hydrocarbon solvent may, to promote more rapid drying, be readily determined by routine experimentation. In general, however, amounts in the range of from about 1 to 30%, preferably 5 to 20%, by weight of the composition will produce useful results.

The heptane solvent (or other volatile non-polar hydrocarbon solvent) is used in conjunction with one or more additional solvents conventionally used in nail enamel compositions and, particularly, the fast drying nail enamel compositions, as well known in the art. The particular solvents will be selected in view of the film forming resins present in the composition and in consideration of the desired drying time.

As examples of suitable solvents mention may be made of, for example, such low boiling solvents as acetone, ethyl acetate, methyl acetate, ethanol, isopropanol, n-butanol, propylacetate, n-butylacetate, amylacetate, and other esters, methychloroform, methylene chloride, methylethylketone and other ketones, diethyl ether, tetrahydrofuran, 1,4-dioxane and other ethers. Individual ones or mixtures of these solvents may be readily selected in varying weight proportions according to need. Also, although generally less preferred higher boiling solvents, for example, cellosolve, butylcellosolve acetate, cellosolve acetate, methyl cellosolve acetate, butyl cellosolve, ethyl cellosolve, and the like, may be included in the solvent mixture, in amounts which do not impede the fast drying property of the composition.

The amount of solvent, including solvent mixtures, other than heptane or other hydrocarbon solvent as set forth above, required to assure both fast drying and acceptable product viscosity (i.e., ease of applying without running) will, of course, depend on the nature of the solvent and the nature and amounts of the other ingredients, such as, in particular resin and other film forming ingredients, thickeners, solids, etc. Usually, however, amounts of solvent(s) suitable for the purpose of this invention will fall within the range of from about 20 to 70% by weight of the composition, preferably, from about 30 to 60% by weight of the composition. It is understood that a portion or even all of the solvents may be incorporated into the enamel composition as solvent solutions of one or more of the non-solvent ingredients, such as, in particular, a solvent solution of nitrocellulose, color solution, etc. Also, the total amount of solvents including heptane or other hydrocarbon solvent should, generally, fall in the range of from about 25% to 90%, preferably from about 35% to 85%, based on the total weight of the composition.

Nitrocellulose is the preferred primary film-forming polymer material in the fast drying nail enamel composition of this invention because of its ready availability and its ability to impact hardness, toughness, resistance to abrasion and ability to release solvent. Suitable examples of nitrocellulose, which are all readily commercially available, include nitrocellulose RS ¼ sec., nitrocellulose RS ½ sec., nitrocellulose SS ¼ sec., nitrocellulose SS ½ sec., nitrocellulose HIG ¼ sec., nitrocellulose HIG ½ sec., and nitrocellulose SL-1. The amount of nitrocellulose will typically fall within the range of from about 1.0 to 25% by weight, preferably 3 or 5 to 20% by weight, based on the total composition.

Other primary film-forming polymers which can contribute the necessary hardness, toughness, abrasion resistance and solvent release characteristics may be used in place of some or all of the nitrocellulose film former. Examples of such film-forming polymers include cellulose derivatives, such as, for example, methyl cellulose, ethyl cellulose, propyl cellulose, butyl cellulose, cellulose phthalate, cellulose acetate propionate, cellulose acetate butyrate, cellulose acetate, hydroxypropyl cellulose, and the like.

The compositions also include a secondary film-forming resin component in order to strengthen the primary film forming component and provide the enamel coating with acceptable gloss and adhesion characteristics. Examples of suitable secondary film-forming polymers are the vinyl polymers such as polyvinyl acetates and butyrates, vinyl chloride/vinyl acetate copolymers, as well as a number of methacrylate and acrylate type polymers and polyester resins. Mention may also be made of arylsulfonamide-formaldehyde resins which have also been used for this purpose, for example, toluene sulfonamide-formaldehyde resin.

The amount of the secondary film-former may be readily determined by routine experimentation depending on the desired characteristics, e.g. gloss, in the final enamel. Generally, however, amounts within the range of from about 2 to 15%, preferably from about 4 to 10% by weight, based on the total composition will provide acceptable results.

A plasticizer or mixture of plasticizers will generally also be included in the nail enamel composition as is customary in the art in order to soften and impart flexibility to the resulting film.

A particularly preferred plasticizer for use in this invention is dibutyl phthalate (DBP) which may be added in amounts ranging from about 1 to 10% by weight, preferably 2 to 8% by weight, especially from about 3 to 5% by weight, based on the total composition.

One or more additional conventional plasticizers usually used together with the nitrocellulose film-former may also be used in combination with the DBP plasticizer. Examples of such plasticizers include camphor, sucrose acetate isobutyrate, triphenyl phosphate, tricresyl phthalate, butyl phthalate, butyl glycolate, dioctyl phthalate, dibutoxy ethyl phthalate, castor oil, benzyl benzoate, tributyl phosphate, butyl acetyl ricinoleate, butyl stearate, triethyl citrate, dibutyl tartarate, diamylphthalate, and the like. Camphor, triphenyl phosphate and dibutyl phthalate, alone or in admixture, are preferred. Amounts of the additional plasticizers will generally range from about 1 to 12% by weight, preferably 2 to 10% by weight, based on the total composition.

Compositions based on the above ingredients, namely, solvent(s), primary and secondary film-forming polymers and resins, plasticizers, and vinyl-silicone copolymer, form fast drying nail enamels. However, although not intending to be bound by any theory of operation, but presumably due to trapping of solvent molecules, migrating out of the film-forming polymer(s), being trapped just under the surface of the enamel which top is surface layer dries most rapidly, bubbles form in the dried enamel coating to ruin the appearance of the coated nails.

Although, as shown in the examples that follow, some commercial antifoam agents are somewhat effective in reducing the bubbling problem, the problem is not eliminated. However, it has been discovered that very small amounts of dimethicone (polydimethylsiloxane) antifoaming agent, such as the commercially available product DC 200 Fluid (350 cSt) is effective in substantially totally eliminating bubble formation.

Suitable antifoaming agents, therefore, include liquid polydimethylsiloxane having a viscosity in the range of from about 200 to 500 cSt, preferably from about 300 to 400 cSt. These antifoaming agents are effective in minor amounts, usually less than about 0.3% by weight, such as from about 0.02 to 0.3%, preferably from about 0.06 to 0.20%, by weight, based on the total composition.

The nail enamel compositions may additionally include any of the usual adjuvant ingredients commonly added to nail enamels, in amounts which do not impair the fast drying properties. For instance, mention may be made of coloring agents, such as pigments, dyestuffs, pearlescent agents and the like; thixotropic agents; fillers; perfumes, preservatives (such as microbicides) antioxidants), UV inhibitors or absorbers, e.g. etocrylene, levelling agents, and the like.

Coloring agents are common nail polish additives to provide cosmetically acceptable shades and to opacify the films.

Pigments for use in the present invention include for example red pigments, including for example, D & C red No. 7, D & C red No. 30, D & C red No. 34. Other pigments which may be used in compositions according to the present invention include the Lake pigments, for example, D & C yellow No. 5 Lake, D & C red No. 6 Lake, D & C red No. 7 Lake, D & C red No. 34 Lake, D & C Red No. 2 Lake, and Ext. D & C Red No. 2 Lake. In addition to the above-named pigments, additional pigments can include cosmetic-grade or purified titanium dioxide (white), mica, bismuth oxychloride, yellow and red iron oxides, iron blue, iron oxi black, ultramarine blue, chromide oxide greens, ferric ammonium ferrocyanide, carbon black or lampblack (generally, in minute quantities).

In addition to the above-named pigments, iridescent additives may be included for example, "pearl essence", such as a suspension of crystalline guanine in nitrocellulose and solvents as well as other additives which will affect the appearance of the pigment. Although the amount of pigment in compositions of the present invention will vary as a function of the type of pigment and other components included in the composition, in general, pigments are included in an amount ranging from about 0.025 to about 4.0% by weight and preferably in an amount ranging from about 0.5 to about 1% by weight of the composition.

When pigments are included in compositions according to the present invention, it is useful to include a thixotropic agent for enhancing the suspension of pigment in the other components of the composition. Although a number of thixotropic agents generally used in the nail enamel art may be used to produce compositions according to the present invention, preferred thixotropic agents include the thixotropic clays, especially stearalkonium hectorites and stearalkonium bentonites. In particularly preferred compositions according to the present invention, thixotropic agent is included in an amount sufficient to produce a gel, preferably a colloidal gel. In general, the pure thixotropic agent without the additives, is included in amounts ranging from about 2% to about 5% by weight of the composition, preferably about 2 to about 4% and most preferably about 2 to 3% by weight of the composition.

In a particularly preferred embodiment of the invention a finely ground (about 5 microns) thixotropic agent (clay) is provided as suspension in a base mixture which additionally includes a solvent solution of plasticizer (camphor) and nitrocellulose. UV inhibitor, e.g., benzophenone, may also be is also present in the base mixture.

The fast drying nail enamel composition may be readily prepared by combining the base mixture with the plasticizer, e.g. dibutyl phthlate, the vinyl-silicone copolymer, optional hydrocarbon solvent, e.g. heptane, coloring agents, and antifoaming dimethicone additive, as well as any other optional additives, in any suitable mixing apparatus as is well known in the art.

REFERENCE EXAMPLE

The following composition was prepared by mixing the following ingredients until homogeneous. While vigorously agitating the Base Mixture the vinyl silicone copolymer is added slowly to avoid lumping. The mixture is stirred until the copolymer is completely dissolved in *the Base Mixture to ensure homogeneity.

|  | (weight %) |
| --- | --- |
| Base Mixture (solvents, heptane, nitrocellulose, clay, camphor, DBP, TPP, UV inhibitor) provided by Kirker Enterprises, Paterson, NJ | 99.5 |
| vinyl-silicone copolymer (Polymer VS-80, from 3M Co.) | 0.5 |

When the above formulation was applied to fingernails (previously cleaned and dried) the resulting enamel coating was allowed to dry for 10 minutes (no residual tack), however severe bubbling was observed to totally impair the usefulness of the product.

EXAMPLE 1

The following commercially available antifoam agents were added in varying amounts to the above formulation (by mixing the appropriate amount of antifoam agent into the formulation for at least 15 minutes) and reapplied to previously cleaned and dried fingernails under the same conditions used in the above test. The results are shown in the following Table.

| ANTIBUBBLING ADDITIVE PERFORMANCE SUMMARY | | |
| --- | --- | --- |
| Additive | Concentration | Result[a] |
| Surfynol 104PA | 1% | 2 |
| Permethyl 99A | 1 | 2 |
| Permethyl 97A | 1 | 1 |
| Shell Sol | 1 | 0 (worse) |
| Butyl Alcohol | 1 | 0 (worse) |
| Dapro U-99 | 1 | 0 |
| Dapro S-65 | 1 | 0 |
| Byketol WS | 2 | 0 |
| Byketol OK | 2 | 0 |
| BYK 396 | 0.04 | 0 |
| BYK 396 | 0.1 | 2 |
| BYK 322 | 0.3 | 0 |
| BYK 325 | 0.5 | 0 |
| Dehydran ARA-7219 | 1 | 0 |
| Perenol F-4-HN | 2 | 1 |
| Surfynol DF-37 | 0.5 | 2 |
| Surfynol DF-58 | 0.5 | 1 |
| Dipropylene Glycol Methyl Ether | 1 | 2 |
| Gamma Butyrolactone | 1 | 1 |
| Tego Wet KL | 1 | 0 |
| Trivent DIA | 1 | 0 |
| Antifoam A (dimethicone) | 1 | 3 |
| Dow Corning 200 Fluid/350 cSt | 0.25 | 3 |
| Dow Corning 344 Fluid | 1 | 2 |
| DC 200/Per. 99A | 0.25/1 | 3 |
| DC 200/Surf. 104PA | 0.25/1 | 2 |
| Surf. 104PA/DF-37 | 1/0.5 | 2 |
| Surf. 104PA/DF-58 | 1/0.5 | 1 |
| Isobutyl Isobutyrate | 1 | 1 |
| 2-Ethyl Hexyl Acetate | 1 | 3 |
| Diisobutyl Ketone | 1 | 2 |
| Dehydran 1620 | 0.5 | 1 |
| Dehydran 1513 | 0.5 | 1 |
| DC 200/0.65 cSt | 1 | 3 |
| DC 200/350 | 0.1 | 3 |

[a]Results were classified as follows:
0 - No effect
1 - Slight reduction in bubbling
2 - Reduction in bubbling
3 - Significant reduction in bubbling

EXAMPLE 2

The following fast-drying, non-bubbling pigmented nail enamel formulation is prepared:

|  | parts by weight |
| --- | --- |
| Ethyl acetate | 30.5 |
| Butyl acetate | 25.0 |
| Isopropyl alcohol | 5.0 |
| Nitrocellulose | 18.0 |
| Polyester film-forming resin | 9.0 |
| Camphor | 1.0 |
| Dibutylphthalate | 5.0 |
| Benzophenone-1 | 0.5 |
| Vinyl-Silicone fast dry copolymer VS-80 | 0.8 |
| Stearalkonium hectorite | 2.0 |
| Pigments | 3.0 |
| Dow Corning 200/350 antifoam | 0.2 |

What is claimed is:

1. A fast-drying, non-bubbling nail enamel composition which comprises a solvent solution of plasticized film-forming cellulose derivative, vinyl-silicone graft or block copolymer comprising a silicone polymer segment and a vinyl polymer segment, and dimethicone anti-foaming agent.

2. The fast-drying, non-bubbling nail enamel composition of claim 1 wherein the vinyl-silicone graft or block copolymer comprises a copolymer of the formula:

$$\begin{array}{c}(R_1)_{3-x}\\ (G_2SR_2)_x\end{array}\!\!\!Si\!-\!(OSi)_y\!-\!OSi\!\!\!\begin{array}{c}G_5\\ |\\ G_6\end{array}\!\!\!\begin{array}{c}(R)_{3-q}\\ (R_4SG_4)_q\end{array}$$

wherein $G_5$ represents monovalent moieties which can independently be the same or different selected from the group consisting of alkyl, aryl, alkaryl, alkoxy, alkylamino, fluoroalkyl, hydrogen and -ZSA;

A represents a vinyl polymeric segment consisting essentially of polymerized vinyl monomer, Z is a divalent linking group, $G_6$ represents monovalent moieties which can independently be the same or different selected from the group consisting of alkyl, aryl, alkaryl, alkoxy, alkylamino, fluoroalkyl, hydrogen, and -ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkylamino, fluoroalkyl, hydrogen and hydroxyl;

$R_4$ can independently be the same or different and are divalent linking groups;

x is an integer of 0–3;

y is an integer of 5 or greater;

q is an integer of 0–3;

wherein at least one of the following is true:

q is an integer of at least 1;

x is an integer of at least 1;

$G_5$ comprises at least one -ZSA moiety; and $G_6$ comprises at least one -ZSA moiety.

3. In a fast-drying nail enamel containing plasticized film-forming agent, the improvement comprising the combination of a fast drying vinyl-silicone graft or block copolymer of the formula $$\begin{array}{c}(R_1)_{3-x}\\ (G_2SR_2)_x\end{array}\!\!\!Si\!-\!(OSi)_y\!-\!OSi\!\!\!\begin{array}{c}G_5\\ |\\ G_6\end{array}\!\!\!\begin{array}{c}(R)_{3-q}\\ (R_4SG_4)_q\end{array}$$

wherein $G_5$ represents monovalent moieties which can independently be the same or different selected from the group consisting of alkyl, aryl, alkaryl, alkoxy, alkylamino, fluoroalkyl, hydrogen and -ZSA;

A represents a vinyl polymeric segment consisting essentially of polymerized vinyl monomer, Z is a divalent linking group, $G_6$ represents monovalent moieties which can independently be the same or different selected from the group consisting of alkyl, aryl, alkaryl, alkoxy, alkylamino, fluoroalkyl, hydrogen, and -ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkylamino, fluoroalkyl, hydrogen and hydroxyl;

$R_4$ can independently be the same or different and are divalent linking groups;

x is an integer of 0–3;

y is an integer of 5 or greater;

q is an integer of 0–3;

wherein at least one of the following is true:

q is an integer of at least 1;

x is an integer of at least 1;

$G_5$ comprises at least one -ZSA moiety; and $G_6$ comprises at least one -ZSA moiety;

and an amount of dimethicone anti-foaming agent effective to prevent bubbling during drying of the enamel coating.

4. The nail enamel according to claim 3 wherein the amount of the vinyl silicone copolymer is from about 0.1 to about 5% by weight of the composition and the amount of the anti-foaming agent is from about 0.02 to about 0.3% by weight.

5. The nail enamel according to claim 3 which further comprises from about 1 to about 30% by weight of volatile non-polar aliphatic hydrocarbon solvent.

6. The nail enamel according to claim 3 wherein the dimethicone anti-foaming agent has a viscosity in the range of from about 200 to 500 cSt.

7. The nail enamel according to claim 3 wherein the film-forming agent comprises a film-forming vinyl polymer.

8. The nail enamel according to claim 3 wherein the film-forming agent comprises a film-forming polyester.

9. The nail enamel according to claim 3 wherein the film-forming agent comprises arylsulfonamide-formaldehyde resin.

10. In a fast-drying nail enamel containing plasticized film-forming agent, the improvement comprising the combination of a fast drying vinyl-silicone graft or block copolymer of the formula $$\begin{array}{c}(R_1)_{3-x}\\ (G_2SR_2)_x\end{array}\!\!\!Si\!-\!(OSi)_y\!-\!OSi\!\!\!\begin{array}{c}G_5\\ |\\ G_6\end{array}\!\!\!\begin{array}{c}(R)_{3-q}\\ (R_4SG_4)_q\end{array}$$

wherein $G_5$ represents monovalent moieties which can independently be the same or different selected from the group consisting of alkyl, aryl, alkaryl, alkoxy, alkylamino, fluoroalkyl, hydrogen and -ZSA;

A represents a vinyl polymeric segment consisting essentially of polymerized vinyl monomer, Z is a divalent linking group, $G_6$ represents monovalent moieties which can independently be the same or different selected from the group consisting of alkyl, aryl, alkaryl, alkoxy, alkylamino, fluoroalkyl, hydrogen, and -ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkylamino, fluoroalkyl, hydrogen and hydroxyl;

$R_4$ can independently be the same or different and are divalent linking groups;

x is an integer of 0–3;

v is an integer of 5 or greater;

q is an integer of 0–3;

wherein at least one of the following is true:

q is an integer of at least 1;

x is an integer of at least 1;

$G_5$ comprises at least one -ZSA moiety; and $G_6$ comprises at least one -ZSA moiety;

and an amount of dimethicone anti-foaming agent effective to prevent bubbling during drying of the enamel coating.

11. The nail enamel according to claim 10 wherein the cellulose derivative is selected from the group consisting of nitrocellulose, methyl cellulose, ethyl cellulose, propyl cellulose, butyl cellulose, cellulose phthalate, cellulose acetate propionate, cellulose acetate butyrate, cellulose acetate and hydroxypropyl cellulose.

12. A nail enamel composition comprising solvent, at least one film forming agent, plasticizer for the film-forming agent, vinyl silicone graft or block copolymer of the formula $$(R_1)_{3-x}(G_2SR_2)_x Si - (OSi)_y \begin{matrix} G_5 \\ | \\ G_6 \end{matrix} - OSi(R)_{3-q}(R_4SG_4)_q$$

wherein $G_5$ represents monovalent moieties which can independently be the same or different selected from the group consisting of alkyl, aryl, alkaryl, alkoxy, alkylamino, fluoroalkyl, hydrogen and -ZSA;

A represents a vinyl polymeric segment consisting essentially of polymerized vinyl monomer, Z is a divalent linking group, $G_6$ represents monovalent moieties which can independently be the same or different selected from the group consisting of alkyl, aryl, alkaryl, alkoxy, alkylamino, fluoroalkyl, hydrogen, and -ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkylamino, fluoroalkyl, hydrogen and hydroxyl;

$R_4$ can independently be the same or different and are divalent linking groups;

x is an integer of 0–3;

y is an integer of 5 or greater;

q is an integer of 0–3;

wherein at least one of the following is true:

q is an integer of at least 1;

x is an integer of at least 1;

$G_5$ comprises at least one -ZSA moiety; and $G_6$ comprises at least one -ZSA moiety;

and an anti-foaming agent in an amount effective to substantially prevent bubbling during drying of the enamel coating.

13. A nail enamel composition according to claim 12 wherein the anti-foaming agent is dimethicone, 2-ethyl hexyl acetate, 2,4,7,9-tetramethyl-5-decyne-4,7-diol, isododecane, cyclic silicone tetramer or dipropylene glycol methyl ether.

* * * * *